(12) United States Patent
Kreymann et al.

(10) Patent No.: US 8,377,308 B2
(45) Date of Patent: Feb. 19, 2013

(54) DIALYSATE REGENERATION UNIT

(75) Inventors: Bernhard Kreymann, München (DE);
Catherine Elisabeth Schreiber,
Riemerling (DE); **Ahmed Nabeel
Al-Chalabi**, München (DE)

(73) Assignee: Hepa Wash GmbH, Garching (DE)

( * ) Notice: Subject to any disclaimer, the term of this patent is extended or adjusted under 35 U.S.C. 154(b) by 503 days.

(21) Appl. No.: 12/741,571

(22) PCT Filed: Dec. 3, 2007

(86) PCT No.: PCT/EP2007/010471
§ 371 (c)(1),
(2), (4) Date: May 5, 2010

(87) PCT Pub. No.: WO2009/071103
PCT Pub. Date: Jun. 11, 2009

(65) Prior Publication Data
US 2010/0258503 A1  Oct. 14, 2010

(51) Int. Cl.
*A61M 1/16* (2006.01)
*A61M 1/34* (2006.01)
*B01D 15/00* (2006.01)
(52) U.S. Cl. ..... 210/639; 210/140; 210/149; 210/195.1; 210/195.2; 210/198.1; 210/198.2; 210/201; 210/202; 210/321.71; 210/504
(58) Field of Classification Search .......... None
See application file for complete search history.

(56) References Cited

U.S. PATENT DOCUMENTS

| 5,744,042 A | 4/1998 | Stange et al. |
| 7,435,342 B2 * | 10/2008 | Tsukamoto ................ 210/195.2 |
| 2005/0082225 A1 | 4/2005 | Kreymann |

FOREIGN PATENT DOCUMENTS

GB   1484642   9/1977

OTHER PUBLICATIONS

Daugirdas, et al., Handbook of Dialysis, 4th Ed., pp. 59-79.
Misra, "The Basics of Hemodialysis Equipment," Hemodialysis International 2005; 9: 30-36.
Polaschegg, et al., "Hemodialysis machines and monitors, in: Replacement of Renal Function by Dialysis", 5th Ed., eds. Horl, Koch, Lindsay, Ronco, Winchester, pp. 325-449.

* cited by examiner

*Primary Examiner* — Krishnan S Menon
*Assistant Examiner* — Dirk Bass
(74) *Attorney, Agent, or Firm* — Klauber & Jackson LLC

(57) ABSTRACT

A dialysate regeneration unit adapted for regenerating a dialysate containing carrier substances comprises a first flow path and a second flow path. The first flow path comprises a first supply unit adapted for adding an acidic fluid to the dialysate flowing in the first flow path, and a detoxification unit located downstream of the first supply unit. The detoxification unit is adapted for removing toxins from the acidified dialysate flowing in the first flow path. The second flow path extends in parallel to the first flow path. The second flow path comprises a second supply unit adapted for adding an alkaline fluid to the dialysate flowing in the second flow path, and a further detoxification unit located downstream of the second supply unit. The further detoxification unit is adapted for removing toxins from the alkalized dialysate flowing in the second flow path.

37 Claims, 3 Drawing Sheets

DIALYSATE REGENERATION UNIT

Figure 1:
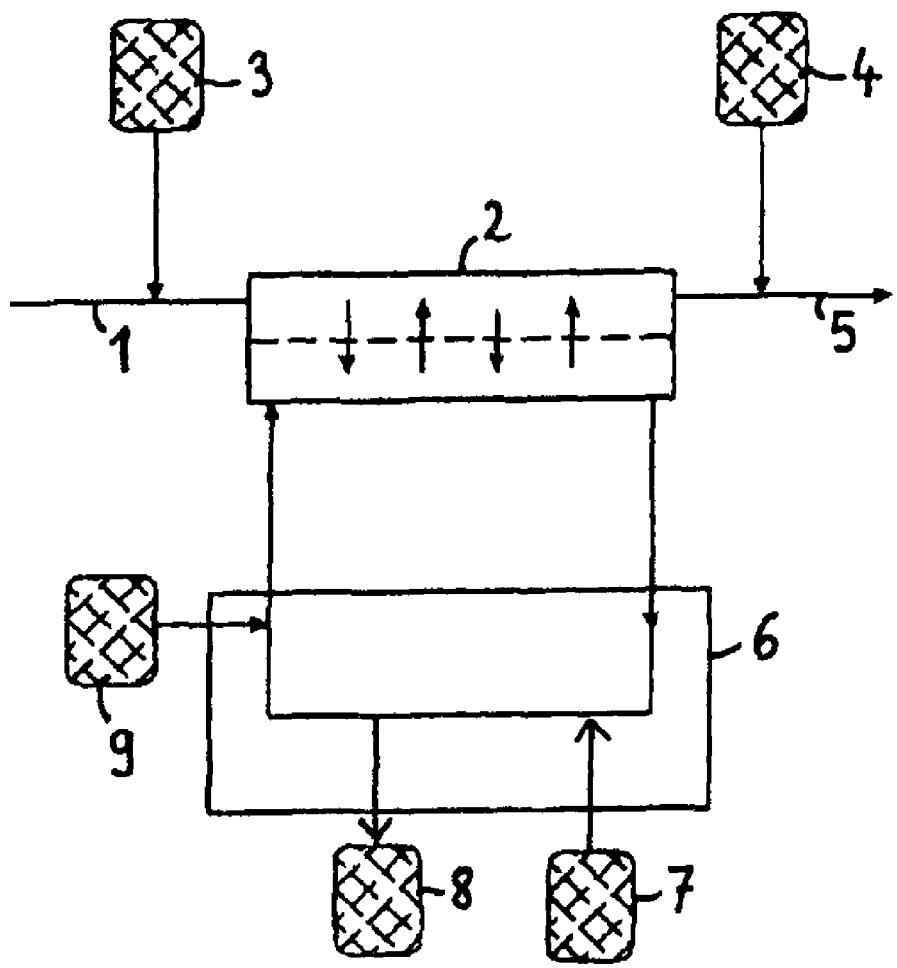

The present invention relates to a dialysate regeneration unit adapted for regenerating a dialysate containing carrier substances. The invention further relates to a dialysis system, and to a method for regenerating a dialysate containing carrier substances.

When liver or kidney of a human being fail to perform their normal functions, inability to remove or metabolise certain substances results in their accumulation in the body. These substances can be differentiated according to their solubility in water: Water-soluble and water-insoluble (or protein-bound). Different extracorporeal procedures are available to help replace the failing functions. Hemodialysis is the gold standard for treating patients with renal failure. For this purpose, a dialyzer is used which is divided into two compartments by a semipermeable membrane. Blood is passed through the blood compartment of the dialyzer separated by the semipermeable membrane from dialysis fluid which passes through the dialysis compartment of said dialyzer. A physiological dialysis fluid should comprise the desired electrolytes, nutrients and buffers in concentrations so that their levels in the patient's blood can be brought to normal.

The routine hemodialysis is of little help for patients with liver failure especially when they have no accompanying renal failure. This is mainly due to the fact that the main toxins like metabolites, e.g. bilirubin, bile acids, copper and other substances like gases, hormones or drugs accumulating in hepatic failure are protein-bound and therefore hardly removed by hemodialysis.

In order to enhance the removal of the protein-bound substances, the dialysis fluid composition is modified to comprise albumin, which binds to the unbound toxins travelling from blood to the dialysate across the semipermeable membrane. The mode of treatment is then called "albumin dialysis". The presence of albumin in the dialysate facilitates the removal of protein-bound substances from blood. The use of albumin is based on its being the main carrier protein for protein-bound toxins in the blood.

However, the commercially available albumin is very expensive. Therefore, albumin-based systems incur high treatment costs. Furthermore, these systems offer an unsatisfactory detoxification efficiency: on average only up to 30% reduction of the bilirubin level as a marker for protein-bound substances can be achieved. Although the albumin-based dialysis processes bring about an improvement in the symptoms of hepatic encephalopathy, a normalization of the values cannot be achieved as a consequence of the limited detoxification efficacy and high treatment costs.

US patent application US 2005/0082225 A1 relates to a means of dialysis for removing protein-bound substances from a biological fluid, especially blood or blood plasma, which contains at least one means for solubilizing protein-binding substances to be removed into the biological fluid and/or dialysis fluid, and to a process for removing protein-bound substances from a biological fluid.

It is an object of the invention to provide an improved apparatus and method for regenerating a dialysate containing carrier substances.

The object of the invention is solved by a dialysate regeneration unit according to claim 1, a dialysis system according to claim 26, and by a method for regenerating a dialysate containing carrier substances according to claim 35.

A dialysate regeneration unit according to embodiments of the present invention, which is adapted for regenerating a dialysate containing carrier substances, comprises a first flow path and a second flow path. The first flow path comprises a first supply unit adapted for adding an acidic fluid to the dialysate flowing in the first flow path, and a detoxification unit located downstream of the first supply unit. The detoxification unit is adapted for removing toxins from the acidified dialysate flowing in the first flow path. The second flow path extends in parallel to the first flow path. The second flow path comprises a second supply unit adapted for adding an alkaline fluid to the dialysate flowing in the second flow path, and a further detoxification unit located downstream of the second supply unit. The further detoxification unit is adapted for removing toxins from the alkalised dialysate flowing in the second flow path.

For dialyzing patients with liver failure, a dialysis fluid containing carrier substances like e.g. albumin is employed. A dialysis fluid of this kind is generally quite expensive. For cleaning and regenerating the dialysis fluid, toxins binding to the carrier substances have to be removed. For efficiently removing said toxins, the dialysate regeneration unit according to embodiments of the present invention comprises two flow paths that are fluidically connected in parallel. The dialysate to be regenerated is split up and conveyed through the two flow paths. In the first flow path, an acidic fluid is added to the dialysate. For toxins that are soluble in acidic solution, the concentration of free toxins in solution is increased. In the detoxification unit located downstream of the acidic fluid supply unit, the free toxins are removed from the acidified dialysate flowing in the first flow path. By adding an acidic fluid to the dialysate, removal of acidic soluble toxins is facilitated. Furthermore, by decreasing the pH, alkaline soluble toxins may e.g. be precipitated and thereby removed from the dialysate fluid.

In the second flow path, which extends in parallel to the first flow path, an alkaline fluid is added to the dialysate flowing in the second flow path. Due to the increase of the pH, the concentration of free alkaline soluble toxins is increased, and thus, removal of alkaline soluble toxins is facilitated. These toxins are removed by a further detoxification unit, which is located downstream of the alkaline fluid supply unit. The further detoxification unit is adapted for removing toxins from the alkalized dialysate flowing in the second flow path. Furthermore, by increasing the pH, acidic soluble toxins may e.g. be precipitated and thereby removed from the dialysate fluid.

By providing an acidic flow path and an alkaline flow path in parallel, both acidic soluble toxins and alkaline soluble toxins may be efficiently removed from the dialysate. Hence, the dialysate regeneration unit according to embodiments of the present invention is capable of efficiently removing protein-binding toxins. The term "toxin" is understood very broadly here and additionally covers all protein-binding substances which normally are not directly referred to as toxins, such as drugs, electrolytes, hormones, fats, vitamins, gases, and metabolic degradation products like bilirubin.

Downstream of the detoxification units, the regenerated acidified dialysate from the first flow path may be merged with the regenerated alkalized dialysate from the second flow path, whereby the acidified dialysis fluid from the first flow path and the alkalized dialysis fluid from the second flow path may neutralize one another at least partially. Hence, by merging the flow of acidified dialysate from the first flow path with the flow of alkalized dialysate from the second flow path, a flow of regenerated dialysate at a physiological pH value may be provided. Furthermore, the exact pH value of the regenerated dialysate may be adjusted by regulating the respective flows conveyed through the first and the second flow path. Hence, the dialysate regeneration unit according to embodiments of the present invention is capable of providing a regenerated dialysis fluid at a physiological pH value.

According to a preferred embodiment, the acidic fluid added by the first supply unit comprises at least one of: hydrochloric acid, sulfuric acid, acetic acid.

Preferably, the alkaline fluid added by the second supply unit comprises at least one of: sodium hydroxide solution, potassium hydroxide solution.

Further preferably, the acidic fluid and the alkaline fluid are chosen such that "physiological" neutralization products are generated during neutralization. For example, a certain concentration of the occurring neutralization products might already be present in the respective biological fluid anyway. For example, when using aqueous hydrochloric acid and aqueous sodium hydroxide solution, a certain concentration of NaCl is produced during neutralization of the acidified flow and the alkalized flow. NaCl is also present in a biological fluid like e.g. blood or blood serum.

In a preferred embodiment, the first supply unit is adapted for adjusting the pH of the dialysate in the first flow path to a pH between 1 and 7, preferably between 2.5 and 5.5.

In a preferred embodiment, the second supply unit is adapted for adjusting the pH of the dialysate in the second flow path to a pH between 7 and 13, preferably between 8 and 13.

According to a preferred embodiment, by decreasing the pH of the dialysate in the first flow path, a concentration ratio of toxin-carrier-complex to free toxin and free carrier substance is shifted in favour of the free toxin for at least some of the toxins in the dialysate, thereby increasing a concentration of free toxins in the dialysate. By decreasing the pH of the dialysate in the first flow path, the solubility of acidic soluble toxins (like e.g. magnesium or copper) is increased, whereas the binding affinity between the acidic soluble toxins and the carrier substances is reduced. Accordingly, the concentration of free toxins in solution is increased.

Further preferably, the detoxification unit is adapted for at least partially removing said free toxins. Due to the increased concentration of free toxins, said toxins may be removed at an increased rate.

Furthermore, by decreasing the pH value of the dialysate in the first flow path, some of the alkaline soluble toxins may e.g. be precipitated and thereby removed from the dialysate fluid.

In a preferred embodiment, by increasing the pH of the dialysate in the second flow path, a concentration ratio of toxin-carrier-complex to free toxin and free carrier substance is shifted in favour of the free toxin for at least some of the toxins in the dialysate, thereby increasing a concentration of free toxins in the dialysate. By increasing the pH of the dialysis fluid in the second flow path, solubility of alkaline soluble substances (like e.g. bilirubin) is increased, whereas the binding affinity between the alkaline soluble toxins and the carrier substances is reduced. Accordingly, the concentration of free toxins in solution is increased.

Preferably, the further detoxification unit is adapted for at least partially removing said free toxins. Due to the increased concentration of free toxins, said toxins may be removed at an increased rate.

Furthermore, by increasing the pH value of the dialysate in the second flow path, some of the acidic soluble toxins may e.g. be precipitated and thereby removed from the dialysate fluid.

According to a preferred embodiment, at least one of the first and the second flow path comprises a temperature regulation unit located upstream of the detoxification unit, e.g. the filtration device, the temperature regulation unit being adapted for increasing or decreasing the temperature of the dialysate. For example, heating or cooling of the dialysate may further enhance the above-described effects.

According to a further preferred embodiment, by increasing the temperature of the dialysate, the concentration ratio of toxin-carrier-complex to free toxin and free carrier substance is shifted in favour of the free toxin for at least some of the toxins in the dialysate, thereby increasing a concentration of free toxins in the dialysate. Accordingly, the free toxins may be removed at an increased rate by the detoxification units.

Preferably, the toxins comprise one or more of: metabolism products, bilirubin, bile acid, drugs, electrolytes like e.g. magnesium, hormones, lipids like e.g. free fatty acids, vitamins, phenols, sulfates, minerals, trace elements like e.g. copper, iron, selenium, manganese, gases like e.g. nitric oxide or carbon monoxide.

Further preferably, the carrier substances comprise one or more of: albumin, human serum albumin, animal albumin, genetically engineered albumin, globulins, lipoproteins, carbon particles. Mixtures containing albumin and at least one further carrier substance are preferred. Moreover, carrier substances may be chosen from substances which change their binding capacity/affinity (e.g. due to a conformational change) to toxins in dependency upon various physico-chemical parameters, e.g. pH and/or temperature and/or light (wavelength) and/or pressure, in particular change their binding capacity to toxins to be removed from the dialysis fluid circuit. Such carrier substances allow the carrier substances to bind to toxins under predetermined conditions, while they may be recycled by modifying the conditions. Under modified conditions the complex of carrier substance and toxin dissociates, which allows the carrier substance to be re-introduced into the dialysis fluid circuit. The toxin is removed by e.g. a precipitation reaction or by the detoxification unit as such, e.g. by diafiltration (s. above). Examples for carrier substances exhibiting the property of (reversibly) binding (dependent on the physico-chemical properties) to a specific toxin may be selected according to the character of the toxin to be bound. In general, glycosides, nucleic acids (and their derivatives), fatty acids, fats, carbon molecules, nanoparticles, memory plastics, memory metals, proteins, resins, secondary plant substances or other complex compounds derived from natural sources, carbon hydrates or synthetic compounds, e.g. polymers, exhibiting this property.

According to a preferred embodiment, the detoxification unit and the further detoxification unit are implemented as regeneration dialyzers, or as ultrafiltration devices, or as diafiltration devices or as devices allowing a precipitation reaction to occur. In case the detoxification units are implemented as dialyzers, toxins may be passed to a discharge fluid via a semipermeable membrane.

In a preferred embodiment, the detoxification unit and the further detoxification unit each comprise a filtration pump and a discharge conduit adapted for withdrawing a discharge fluid from the respective detoxification unit. In the detoxification units, the toxins are passed to the discharge fluid. In the discharge fluid, the toxin concentration is increased, whereas in the dialysate, the toxin concentration is reduced.

Preferably, the first flow path comprises a first pump adapted for pumping the dialysate through the first flow path, and the second flow path comprises a second pump adapted for pumping the dialysate through the second flow path, the first and the second pump operating independently of one another. Flow characteristics in the first flow path may differ from flow characteristics in the second flow path. For example, in an acidic environment, a carrier substance like albumin may have a different shape than in an alkaline environment. As a consequence, the flow resistance in the first flow path may differ from the flow resistance in the second flow path. By providing two separate pumps, these differences may be compensated for, and an equal flow of dialysis fluid in the first and the second flow path may be accomplished.

According to a preferred embodiment, the acidified dialysate supplied by the first flow path is merged with the alkalised dialysate supplied by the second flow path. Downstream of the supply units and the detoxification units of the first and the second flow path, the two flows are merged, and a unified flow of regenerated dialysis fluid is generated.

Further preferably, when the acidified dialysate supplied by the first flow path is merged with the alkalised dialysate supplied by the second flow path, the acidified dialysate and the alkalised dialysate neutralize each other at least partially.

According to a preferred embodiment, the dialysate regeneration system comprises a plurality of switching valves.

Preferably, during a first phase of operation, the switching valves are set such that a first detoxification unit is included in the first flow path and that a second detoxification unit is included in the second flow path, whereas during a second phase of operation, the switching valves are set such that the second detoxification unit is included in the first flow path and that the first detoxification unit is included in the second flow path.

Preferably, the switching valves are operated such that the acidified dialysate is alternatingly supplied to a first detoxification unit and to a second detoxification unit, whereas the alkalised dialysate is alternatingly supplied to the second detoxification unit and to the first detoxification unit.

During the first phase of operation, the first detoxification unit is exposed to a flow of acidic fluid. During this phase of operation, acidic soluble substances, like e.g. magnesium, may be removed from the dialysate. However, other substances, which are insoluble in an acidic environment, might be precipitated during the first phase of operation and thereby removed from the dialysis fluid. The second detoxification unit is exposed to an alkaline environment during the first phase of operation. Accordingly, alkaline soluble substances, like e.g. bilirubin, may be removed from the dialysate and substances that are insoluble in alkaline solution may be precipitated in the second detoxification unit. Precipitation of insoluble substances may impair proper functioning of the detoxification units. For example, precipitated substances may lead to clogging of the detoxification units. Hence, it is proposed that during a second phase of operation, the switching valves are set such that the first detoxification unit and the second detoxification unit are interchanged. Now, the second detoxification unit is included in the first flow path, and the first detoxification unit is included in the second flow path. Accordingly, the first detoxification unit is exposed to an alkaline environment, and acidic insoluble substances that have been precipitated during the first phase of operation may be solubilized and removed from the dialysis fluid. Vice versa, the second detoxification unit is exposed to an acidic environment, which implies that alkaline insoluble substances that have been precipitated during the first phase of operation can be dissolved and removed from the second detoxification unit. By periodically exchanging the first and the second detoxification unit, precipitated substances can be removed, and proper functioning of the detoxification units is ensured over a long period of time. Thus, the life span of the detoxification units is prolongated and the removal of toxins from the dialysate is increased.

According to a preferred embodiment, the switching valves are switched periodically. Thus, an accumulation of precipitated substances is avoided.

Further preferably, the switching valves are automatically switched at regular time intervals, preferably every 30 to 60 minutes. For example, the dialysate regeneration unit might comprise an electronic control unit adapted for controlling operation of the switching valves.

A dialysis system according to embodiments of the present invention comprises a biological fluid circuit, a dialysate circuit, at least one dialyzer, and a dialysate regeneration unit as described above.

In a preferred embodiment, the biological fluid is blood or blood plasma.

In a preferred embodiment, the dialysis system comprises a dialysate reservoir, that is part of the dialysate circuit, wherein the dialysate regeneration unit is adapted for withdrawing dialysate from the dialysate reservoir, for regenerating the dialysate, and for resupplying the regenerated dialysate to the dialysate reservoir.

The dialysate reservoir may act as a buffer reservoir between the blood cleaning circuit and the dialysate regeneration unit. The supply of dialysate to one or more dialyzers of the blood cleaning circuit may be implemented either from the dialysate reservoir or directly from the regeneration circuit, e.g. by splitting the regenerated dialysate flow into two conduits—the first leading to the dialysate reservoir and the second leading to the dialyzers of the blood cleaning circuit. By providing a dialysate reservoir, the dialysate circuit may be decoupled from the dialysate regeneration unit. For example, the flow rate in the dialysate circuit may be chosen independently of the flow rate through the dialysate regeneration unit. In particular, the flow rate in the dialysate regeneration unit may e.g. be higher than the flow rate in the blood cleaning circuit. Furthermore, in the dialysate regeneration unit, cleaning of the dialysate may be carried out under non-physiological operating conditions. By providing a dialysate reservoir and decoupling the dialysate regeneration unit from the blood cleaning circuit, an efficient protection of the patient's blood is accomplished.

According to a preferred embodiment, the dialysate regeneration unit is part of a separate dialysate regeneration circuit.

According to a further preferred embodiment, the regeneration unit is adapted for regenerating the dialysate in a continuous operation or in an intermittent operation. Due to the presence of the dialysate reservoir, an intermittent operation of the dialysate regeneration unit is possible.

According to an alternative embodiment, the dialysate regeneration unit is integrated into the dialysate circuit. In this embodiment, the flow of regenerated dialysate is directly supplied to the dialyzers.

Preferably, the dialyzer comprises a biological fluid compartment that is part of the biological fluid circuit, a dialysate compartment that is part of the dialysate circuit, and a semipermeable membrane separating the biological fluid compartment and the dialysate compartment.

The dialysis system further comprises a substitution unit adapted for supplying substitution fluid to the biological fluid or to the dialysate. For example, by adding substitution fluid, the volume of the biological fluid or dialysate may be increased. Furthermore, the substitution fluid may comprise substances like e.g. electrolytes, nutrients, buffer, and other important substances, which may not have the appropriate concentrations in the biological fluid or in the dialysate. The physiological dialysis fluid and the substitution fluid should complement one another, whereby the aim is that the cleaned blood returned to the patient has electrolytes, nutrients, buffers, and other important substances in physiological concentrations.

Figure 2A:
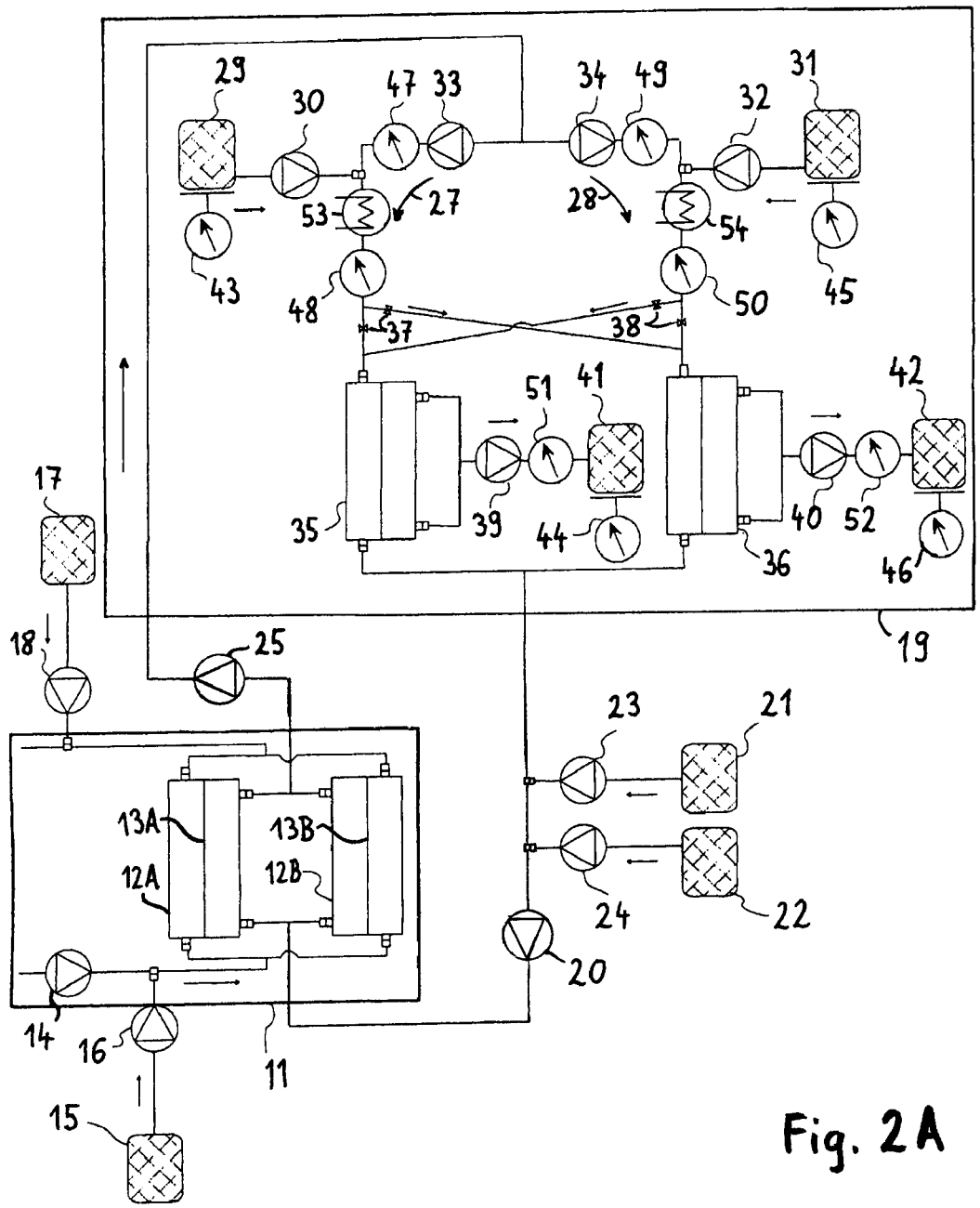
Figure 2B:
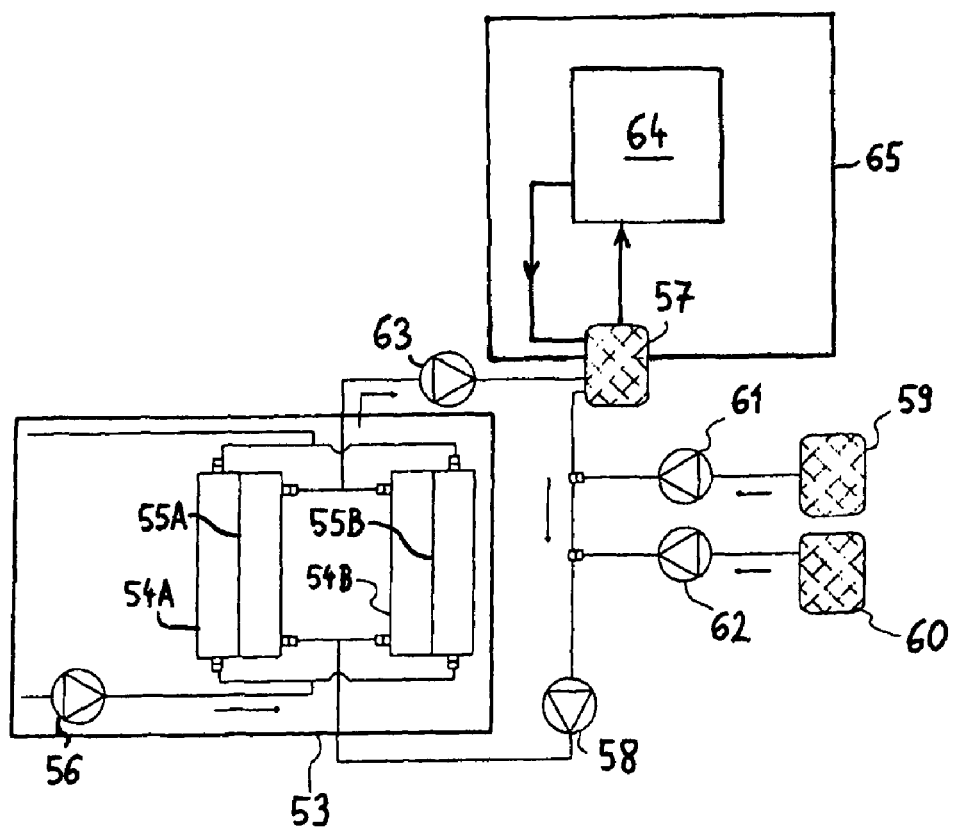

For a better understanding of the present invention and to show how the same may be carried into effect, reference will now be made by way of example to the accompanying drawings in which FIG. 1 is a schematic block diagram of a dialysis system according to an embodiment of the present invention;

FIG. 2A is a more detailed view of a dialysis system according to an embodiment of the present invention, and FIG. 2B shows another embodiment of the invention, wherein the dialysis system comprises a dialysate reservoir.

FIG. 1 shows a schematic block diagram of a dialysis system according to an embodiment of the present invention. Via an arterial blood line 1, blood from a patient is supplied to a dialyzer 2. Before the blood is supplied to the dialyzer 2, a predilution fluid 3 is added to the blood. In the dialyzer 2, the respective flows of blood and dialysate may be conducted in concurrent flow, as shown in FIG. 1. Alternatively, the respective flows of blood and dialysate may be conducted in counterflow. At the dialyzer 2, diffusion, convection and/or ultrafiltration processes take place, and the patient's blood is cleaned. After the blood has passed the dialyzer 2, a postdilution fluid 4 is added to the cleaned blood. The cleaned blood is resupplied to the patient via a venous blood line 5.

The dialysis system comprises a dialysate regeneration circuit 6 adapted for regenerating dialysate that has passed through the dialyzer 2. In embodiments of the present invention, a dialysate that contains carrier substances like e.g. albumin is used. In particular, the dialysate regeneration circuit 6 is adapted for removing protein-binding toxins like e.g. bilirubin, bile acid, etc. from the dialysate. First, one or more fluids 7 are added to the dialysate. Then, fluids 8 are removed from the dialysate, e.g. by filtration, diafiltration, precipitation or dialysis under certain pH and temperature conditions. Furthermore, one or more substitution fluids 9 may be added to correct the concentration of the electrolytes and other important substances in the dialysate. From the dialysate regeneration circuit 6, a flow of regenerated dialysate is supplied to the dialyzer 2.

FIG. 2A gives a more detailed view of an embodiment of a dialysis system according to the present invention.

The dialysis system comprises a blood circuit 11 with two dialyzers 12A and 12B. Each of the dialyzers 12A and 12B comprises a blood compartment, a dialysate compartment, and a semipermeable membrane 13A, 13B that separates the compartments. The dialyzers 12A, 12B are fluidically connected in parallel. Blood from the patient is passed through the tubings via a blood pump 14. Before the blood is supplied to the dialyzers 12A, 12B, a predilution fluid 15 is added to the blood via a predilution pump 16. Then, the blood is passed through the blood compartments of the dialyzers 12A, 12B. Before the cleaned blood is returned to the patient, a postdilution fluid 17 is added to the blood via a postdilution pump 18.

Blood flow rates can be between 100-600 ml/min but are preferably between 150-400 ml/min, more preferably between 150-250 ml/min. Predilution flow rates can be between 1-20 l/h but are preferably between 4-7 l/h. Postdilution flow rates can be between 5-30% of the chosen blood flow rates, but are preferably between 10-20%.

In the embodiment shown in FIG. 2A, the dialysate circuit comprises a dialysate regeneration unit 19. Dialyzing fluid that has been passed through the dialysate regeneration unit 19 is pumped into the dialysate compartments of the dialyzers 12A, 12B with a first dialysate pump 20 at a flow rate between 150-2000 ml/min but preferably between 500-1100 ml/min. In order to bring the electrolytes and other important substances to desired concentrations, substitution fluids 21, 22 may be supplied to the dialysate via respective pumps 23, 24. After passing through the dialysate compartments of the dialyzers 12A, 12B, the dialyzing fluid with the added fluids taken from the patient to reduce his volume overload are transported to the dialysate regeneration unit 19 via a second dialysate pump 25.

According to embodiments of the present invention, the dialysate regeneration unit 19 comprises two flow paths 27, 28 that are fluidically connected in parallel. In flow path 27, which will further on be referred to as the "acidic flow path", an acidic solution 29 comprising a strong acid is added to the dialysis fluid via an acid pump 30. In flow path 28, which will further on be referred to as the "alkaline flow path", an alkaline solution 31 comprising a strong base is added to the dialysis fluid via a base pump 32.

The dialysate regeneration unit 19 comprises two regeneration pumps 33, 34 for transporting the dialysate through the two flow paths 27, 28. Preferably, two separate pumps are used for the transport of the dialysis fluid, because the resistance of the fluid can be different in the acidic flow path 27 and in the alkaline flow path 28. For example, a carrier substance like e.g. albumin might have a different shape in acidic or alkaline conditions and therefore different flow characteristics for different pH values. Alternatively to two pumps, a system with clamps and fluid measurements can be used to achieve constant flow rates in the two flow paths 27 and 28.

Each of the two flow paths 27, 28 comprises a detoxification unit 35, 36 adapted for filtering or dialysing the dialysate, and for removing toxins from the dialysate. The detoxification units 35, 36 might e.g. be implemented as regeneration dialyzers, ultrafiltration units, diafiltration units, etc. The regeneration pump 33 of the acidic flow path 27 and the regeneration pump 34 of the alkaline flow path 28 transfer the dialysate downstream to one of two detoxification units 35, 36 of the dialysate regeneration unit 19. The dialysate is supplied to the detoxification units 35, 36 via a valve mechanism comprising switching valves 37, 38.

In the detoxification unit through which alkaline solution is flowing, alkaline soluble toxins like e.g. bilirubin can be removed by filtration or dialysis. Under alkaline conditions, the concentration of alkaline soluble toxins in solution is increased. Due to this concentration increase of free toxins, removal of the free toxins is facilitated.

In the other detoxification unit through which acidic solution is flowing, these alkaline soluble toxins may e.g. be precipitated and thereby removed from the dialysis fluid.

With regard to acidic soluble toxins like e.g. magnesium, a similar effect is observed. In an acidic solution, the concentration of acidic soluble toxins in solution is increased, and hence, acidic soluble toxins may be removed at an increased rate. In contrast, in the detoxification unit through which alkaline solution is flowing, the acidic soluble toxins are precipitated, e.g. as magnesium hydroxide, and thereby removed from the dialysis fluid.

The switching valves 37, 38 are adapted for changing the direction of the acidified dialysis fluid transported by the regeneration pump 33 on the acidic side either towards the detoxification unit 35 or towards the detoxification unit 36 (switching valves 37) and changing the direction of the alkalised dialysis fluid transported by the regeneration pump 34 on the alkaline side either towards the detoxification unit 36 or towards the detoxification unit 35 (switching valves 38). The switching valves 37, 38 change the direction of flow e.g. every 30-60 minutes so that each detoxification unit 35, 36 receives fluid from one of the regeneration pumps 33 and 34 at a time. However, change of direction of flow may occur every 1 to 60 min depending on the acid used and the mechanism applied. Switching may be performed automatically or individually be the user. Change of direction very 1 to 10, preferably every 1 to 5 min may be preferred for certain applications.

Depending on the filtration type, the precipitated substances can cause an occlusion of the detoxification units 35, 36 by blocking the pores of the detoxification unit 35, 36. To avoid this, the detoxification units 35, 36 are alternated: the detoxification unit that is in one time period (e.g. for 30 min) the acidic detoxification unit is in the following time period (e.g. 30 min) used in the alkaline flow path. This means that then precipitated substances are solved and removed with high concentration by filtration or dialysis. This also enables continuous use of the detoxification units over a long time period.

The switching of the detoxification units 35, 36 may e.g. be done manually, or by a valve mechanism that is electronically controlled. The switching may be performed at different locations in the fluid circuit, the most preferable location being directly upstream of the detoxification units 35, 36. However, the temperature regulation unit 53, 54 may be located in the circuit and/or controlled in a way, which allows them to be included into the switching mechanism acting on the detoxification units. The change of the direction of the e.g. acidified dialysis fluid may be established together with the change of direction of the acidified fluid in the detoxification units 35, 36. However, an independent change of direction of the e.g. acidified dialysis fluid in the temperature regulation units 53, 54 and the detoxification units 35, 36 may also be realized. By including the temperature regulation units in the switching mechanism, it is ensured that the both units do not accumulate precipitated carrier substances, e.g. albumin, which may be caused by exclusively contacting the temperature regulation units 53, 54 with either alkalised or acidified dialysis fluid, in particular due to temperature effects at this unit.

For removing fluids and toxins from the detoxification units 35, 36, the system comprises two filtrate pumps 39, 40 operative to remove discharge fluids 41, 42 from the detoxification units 35, 36. For balancing the volumes of the different fluids, the system may comprise a plurality of scales 43-46 adapted for constantly measuring the fluid volume of the added acid 29, of the added base 31 and of the discharge fluids 41, 42.

Downstream of the detoxification units 35, 36, the flow of regenerated acidified dialysate obtained at the outflow of one of the detoxification units is merged with the flow of regenerated alkalised dialysate obtained at the outflow of the other detoxification unit. By merging the acidified flow with the alkalised flow, the acid and the base neutralize each other, and a flow of regenerated dialysate with a pH in the physiological range between 6 and 8 is generated. The regenerated dialysate may be supplied to the dialyzers 12A, 12B. A temperature regulation unit may be located in the dialysis fluid circuit before the dialysate passes to the dialyzers 12A, 12B. This allows the recycled dialysis fluid to be adjusted to the temperature needed for contacting the blood at the membrane of the dialyzers 12A, 12B.

Preferably, in the acidic flow path 27 and in the alkaline flow path 28, acids or bases are added whose conjugate bases or acids are ions that occur naturally in the human organism. Thus, it is made sure that the regenerated dialysate obtained by merging the acidified flow of dialysate and the alkalised flow of dialysate does not contain any non-physiological substances.

Various system parameters like e.g. pH value, temperature, and conductivity of the dialysate are monitored via sensors 47-50 located on the base and the acid side upstream of the detoxification units 35, 36. In the acidic flow path 27, sensors 47 monitor the system parameters before adding the acid and sensors 48 measure the system parameters after adding the acid. Accordingly, in the alkaline flow path 28, sensors 49 monitor the system parameters before adding the base and sensors 50 measure the system parameters after adding the base.

The system may comprise further sensor units 51, 52 located in the discharge flow paths of the detoxification units 35, 36. The sensor units 51, 52 are adapted for monitoring system parameters like e.g. pH value, temperature and conductivity.

In each of the flow paths 27, 28, further process steps for at least temporarily increasing the concentration of free toxins in the dialysate may be realized, in order to enhance the removal of toxins. These process steps may e.g. include one or more of the following: heating or cooling the dialysate, irradiating the dialysate with waves, changing the salt content of the dialysate, adding a dialysable substance binding to the toxins to be removed.

In the embodiment shown in FIG. 2A, each of the flow paths 27, 28 comprises a respective temperature regulation unit 53, 54. For example, heating of the dialysate may be helpful for weakening the bond between the protein-binding toxins and the carrier substances. The heating may e.g. be effected via direct heating of the fluidfilled tubing system, or by irradiation with microwaves or infrared. Alternatively, the temperature regulation units may be adapted for cooling the dialysate. By changing the temperature of the dialysis fluid, the concentration of free toxins in solution is increased and accordingly, removal of toxins is enhanced.

Another possible process step for changing the concentration ratio of toxin-carrier-complex to free toxin and free carrier substance is to irradiate the dialysate with waves. For example, an ultrasonic apparatus may be used as the device for irradiating with waves. Other appropriate devices may e.g. be those suitable for generating light waves, ultraviolet waves, infrared waves, radio waves and microwaves.

Another possible process step for changing the concentration ratio of toxin-carrier-complex to free toxin and free carrier substance is to change the salt content of the dialysate. Changing the salt concentration may help to solubilize the toxins to be removed. Moreover, it can also be used to restore the binding capacity of recycled carrier substances for toxins. The addition of urea may be necessary to improve the binding capacity of the carrier substances.

Another possible process step for changing the concentration ratio of toxin-carrier-complex to free toxin and free carrier substance is to add dialysable compounds to the dialysate, said dialysable compounds being adapted to bind to the toxins to be removed. Binding compounds which can be used are dialysable compounds of low/intermediate molecular weight that are distinguished by a strong affinity for the substances to be removed. The preferred compounds include caffeine, which binds to bilirubin, and common chelating agents like penicillamine, trientine, deferoxamine, preferiprone, HBED, vitamin C, BAL, DMPS or DMSA, which bind to metal cations such as copper ions or iron ions.

FIG. 2B shows an alternative embodiment of a dialysis system. The dialysis system comprises a blood circuit 53 with two dialyzers 54A and 54B. Each of the dialyzers 54A and 54B comprises a blood compartment, a dialysate compartment, and a semipermeable membrane 55A, 55B that separates the compartments. The dialyzers 54A, 54B are fluidically connected in parallel. Blood from the patient is pumped through the blood compartments of the dialyzers 54A, 54B by a blood pump 56.

The embodiment of FIG. 2B comprises a dialysate reservoir 57 for storing regenerated dialysate. Dialysis fluid from the dialysate reservoir 57 is pumped through the dialysate compartments of the dialyzers 54A, 54B by a first dialysate pump 58. In order to bring the electrolytes and other important substances to desired concentrations, substitution fluids 59, 60 may be supplied to the dialysate via respective pumps 61, 62. After passing through the dialysate compartments of the dialyzers 54A, 54B, the dialyzing fluid with the added fluids taken from the patient are supplied to the dialysate reservoir 57 via a second dialysate pump 63.

From the dialysate reservoir 57, a flow of dialysate is provided to a dialysate regeneration unit 64. The internal set-up of the dialysate regeneration unit 64 is identical to the internal set-up of the dialysate regeneration unit 19 shown in FIG. 2A. The dialysate regeneration unit 64 comprises two flow paths, an acidic flow path and an alkaline flow path, which are fluidically connected in parallel. Each of the flow paths comprises a detoxification unit.

In the embodiment shown in FIG. 2B, a separate dialysate regeneration circuit 65 is provided for regenerating the dialysis fluid contained in the dialysate reservoir 57.

The dialysate regeneration circuit 65 (tertiary circuit) is decoupled from the blood cleaning circuit. The blood cleaning circuit comprises the blood circuit 53 (primary circuit) and the dialysate circuit (secondary circuit). By decoupling the dialysate regeneration circuit from the dialysate circuit, system parameters like flow, temperature and pH are independently adjustable to the needs of the two different processes. For example, dialysate flow during the blood cleaning process may be between 150-2000 ml/min, whereas during the regeneration process, dialysate flow may be between 250-5000 ml/min, preferably between 1000-2000 ml/min. It may be useful to decouple the two circuits by a dialysate reservoir, as in the dialysate regeneration unit the dialysis fluid has non-physiological pH and temperature values which would result in great damage to the patient's blood. The dialysis fluid contained in the dialysate reservoir 57 may either be cleaned in a continuous operation or in an intermittent operation.

The invention claimed is:

1. A dialysate regeneration unit (19, 64) for regenerating a dialysate containing carrier substances, with
    a first flow path (27) comprising
        a first supply unit adapted for adding an acidic fluid (29) to the dialysate flowing in the first flow path (27),
        a detoxification unit located downstream of the first supply unit, the detoxification unit being adapted for removing toxins from the acidified dialysate flowing in the first flow path (27),
    a second flow path (28) that extends in parallel to the first flow path (27), the second flow path (28) comprising
        a second supply unit adapted for adding an alkaline fluid (31) to the dialysate flowing in the second flow path (28),
        a further detoxification unit located downstream of the second supply unit, the further detoxification unit being adapted for removing toxins from the alkalised dialysate flowing in the second flow path (28).

2. The dialysate regeneration unit of claim 1, wherein the acidic fluid added by the first supply unit comprises at least one of: hydrochloric acid, sulfuric acid, acetic acid.

3. The dialysate regeneration unit of claim 1, wherein the alkaline fluid added by the second supply unit comprises at least one of: sodium hydroxide solution, potassium hydroxide solution.

4. The dialysate regeneration unit of claim 1, wherein the first supply unit is adapted for adjusting the pH of the dialysate in the first flow path to a pH between 1 and 7, preferably between 2.5 and 5.5.

5. The dialysate regeneration unit of claim 1, wherein the second supply unit is adapted for adjusting the pH of the dialysate in the second flow path to a pH between 7 and 13, preferably between 8 and 13.

6. The dialysate regeneration unit of claim 1, wherein by decreasing the pH of the dialysate in the first flow path, a concentration ratio of toxin-carrier-complex to free toxin and free carrier substance is shifted in favour of the free toxin for at least some of the toxins in the dialysate, thereby increasing a concentration of free toxins in the dialysate.

7. The dialysate regeneration unit of claim 6, wherein the detoxification unit is adapted for at least partially removing said free toxins.

8. The dialysate regeneration unit of claim 1, wherein by increasing the pH of the dialysate in the second flow path, a concentration ratio of toxin-carrier-complex to free toxin and free carrier substance is shifted in favour of the free toxin for at least some of the toxins in the dialysate, thereby increasing a concentration of free toxins in the dialysate.

9. The dialysate regeneration unit of claim 8, wherein the further detoxification unit is adapted for at least partially removing said free toxins.

10. The dialysate regeneration unit of claim 1, wherein at least one of the first and the second flow path comprises a temperature regulation unit located upstream of the detoxification unit, the temperature regulation unit being adapted for increasing or decreasing the temperature of the dialysate.

11. The dialysate regeneration unit of claim 10, wherein by changing, e.g. increasing, the temperature of the dialysate, the concentration ratio of toxin-carrier-complex to free toxin and free carrier substance is shifted in favour of the free toxin for at least some of the toxins in the dialysate, thereby increasing a concentration of free toxins in the dialysate.

12. The dialysate regeneration unit of claim 1, wherein the toxins comprise one or more of: metabolism products, bilirubin, bile acid, drugs, electrolytes, hormones, lipids, vitamins, phenols, sulfates, trace elements, minerals, gases.

13. The dialysate regeneration unit of claim 1, wherein the carrier substances comprise one or more of: proteins, e.g. albumin, human serum albumin, animal albumin, genetically engineered albumin, globulins, lipoproteins; carbon particles glycosides; nucleic acids (and their derivatives); fatty acids; fats; carbon molecules; nanoparticles; memory plastics; memory metals; resins; secondary plant substances or other complex compounds derived from natural sources; carbon hydrates or synthetic compounds, e.g. polymers.

14. The dialysate regeneration unit of claim 1, wherein the detoxification unit and the further detoxification unit are implemented as regeneration dialyzers, or as ultrafiltration devices, or as diafiltration devices.

15. The dialysate regeneration unit of claim 1, wherein the detoxification unit and the further detoxification unit each comprise a filtration pump and a discharge conduit adapted for withdrawing a discharge fluid from the respective detoxification unit.

16. The dialysate regeneration unit of claim 1, wherein the first flow path comprises a first pump adapted for pumping the dialysate through the first flow path, and wherein the second flow path comprises a second pump adapted for pumping the dialysate through the second flow path, the first and the second pump operating independently of one another.

17. The dialysate regeneration unit of claim 1, wherein the acidified dialysate supplied by the first flow path is merged with the alkalised dialysate supplied by the second flow path.

18. The dialysate regeneration unit of claim 1, wherein, when the acidified dialysate supplied by the first flow path is merged with the alkalised dialysate supplied by the second flow path, the acidified dialysate and the alkalised dialysate neutralize each other at least partially.

19. The dialysate regeneration unit of claim 1, wherein by merging the acidified dialysate supplied by the first flow path with the alkalised dialysate supplied by the second flow path, a flow of regenerated dialysate with a pH value between 6 and 8, further preferably between 6.9 and 7.6, is obtained.

20. The dialysate regeneration unit of claim 19, further comprising at least one sensor unit adapted for determining a pH value of the flow of regenerated dialysate.

21. The dialysate regeneration unit of claim 1, wherein the dialysate regeneration system comprises a plurality of switching valves.

22. The dialysate regeneration unit of claim 21, wherein
during a first phase of operation, the switching valves are set such that a first detoxification unit is included in the first flow path and that a second detoxification unit is included in the second flow path,
whereas during a second phase of operation, the switching valves are set such that the second detoxification unit is included in the first flow path and that the first detoxification unit is included in the second flow path.

23. The dialysate regeneration unit of claim 21, wherein the switching valves are operated such that the acidified dialysate is alternatingly supplied to a first detoxification unit and to a second detoxification unit, whereas the alkalised dialysate is alternatingly supplied to the second detoxification unit and to the first detoxification unit.

24. The dialysate regeneration unit of claim 21, wherein the switching valves are switched periodically.

25. The dialysate regeneration unit of claim 21, wherein the switching valves are automatically switched at regular time intervals, preferably every 1 to 60 minutes.

26. A dialysis system comprising
a biological fluid circuit (11, 53),
a dialysate circuit,
at least one dialyzer (12A, 12B, 54A, 54B),
a dialysate regeneration unit (19, 64) according to claim 1.

27. The dialysis system of claim 26, wherein the biological fluid is blood or blood plasma.

28. The dialysis system of claim 26, further comprising a dialysate reservoir that is part of the dialysate circuit, wherein the dialysate regeneration unit is adapted for withdrawing dialysate from the dialysate reservoir, for regenerating the dialysate, and for resupplying the regenerated dialysate to the dialysate reservoir.

29. The dialysis system of claim 28, wherein the dialysate regeneration unit is part of a separate dialysate regeneration circuit.

30. The dialysis system of claim 28, wherein the regeneration unit is adapted for regenerating the dialysate in a continuous operation or in an intermittent operation.

31. The dialysis system of claim 26, wherein the dialysate regeneration unit is integrated into the dialysate circuit.

32. The dialysis system of claim 26, wherein the dialyzer comprises a biological fluid compartment that is part of the biological fluid circuit, a dialysate compartment that is part of the dialysate circuit, and a semipermeable membrane separating the biological fluid compartment and the dialysate compartment.

33. The dialysis system of claim 26, further comprising a substitution unit adapted for supplying substitution fluid to the biological fluid or to the dialysate.

34. The dialysis system of claim 33, wherein the substitution fluid comprises one or more of: electrolyte, nutrient, buffer.

35. A method for regenerating a dialysate containing carrier substances, the method comprising
splitting a flow of dialysate into a first flow and a second flow,
adding an acidic fluid (29) to the first flow of dialysate,
removing toxins by filtrating, dialysing, precipitating or diafiltrating the acidified first flow of dialysate,
adding an alkaline fluid (31) to the second flow of dialysate,
removing toxins by filtrating, dialysing, precipitating or diafiltrating the alkalized second flow of dialysate,
merging the first and the second flow of dialysate.

36. The method of claim 35, further comprising
periodically switching a plurality of switching valves such that the flow of acidified dialysate is alternatingly supplied to a first detoxification unit and to a second detoxification unit, whereas the flow of alkalized dialysate is alternatingly supplied to the second detoxification unit and to the first detoxification unit.

37. The method of claim 35, further comprising one or more of the following:
regulating the temperature of the acidified dialysate;
removing toxins by precipitation due to the acidification;
regulating the temperature of the alkalized dialysate;
removing toxins by precipitation due to the alkalization.

* * * * *